(12) United States Patent
Himmler et al.

(10) Patent No.: US 8,729,275 B2
(45) Date of Patent: May 20, 2014

(54) PROCESS FOR PREPARING DITHIINE-TETRACARBOXY-DIIMIDES

(75) Inventors: Thomas Himmler, Odenthal (DE); Martin Kaussman, Köln (DE)

(73) Assignee: Bayer CropScience AG, Monheim (DE)

( * ) Notice: Subject to any disclaimer, the term of this patent is extended or adjusted under 35 U.S.C. 154(b) by 134 days.

(21) Appl. No.: 13/112,680

(22) Filed: May 20, 2011

(65) Prior Publication Data

US 2012/0022270 A1    Jan. 26, 2012

Related U.S. Application Data

(60) Provisional application No. 61/348,355, filed on May 26, 2010.

(30) Foreign Application Priority Data

May 21, 2010   (EP) ..................................... 10163519

(51) Int. Cl.
*C07D 495/14*   (2006.01)
*C07D 207/18*   (2006.01)

(52) U.S. Cl.
USPC .......................................... 548/431; 548/565

(58) Field of Classification Search
None
See application file for complete search history.

(56) References Cited

U.S. PATENT DOCUMENTS

| | | |
|---|---|---|
| 3,364,229 A | 1/1968 | Draber et al. |
| 2010/0120884 A1 | 5/2010 | Seitz et al. |

FOREIGN PATENT DOCUMENTS

| | | |
|---|---|---|
| JP | 10-251265 A | 9/1998 |
| PL | 143 804 | 11/1988 |

OTHER PUBLICATIONS

Gaina, Designed Monomers and Polymers, vol. 8(4), pp. 347-363 (2005).*
Draber, W., "Synthese von 1,4-Dithiinen aus Derivaten des Maleinimids," *Chem. Ber. 100*:1559-1570, Verlag Chemie, Germany (1967).
Gaina, C., et al., "Polyimides containing 1,4-dithiine units and their corresponding thiophene 2,3,4,5 tetracarboxylimide units," *High Perform. Polym. 11*:185-195, IOP Publishing Ltd., United Kingdom (1999).
Gaina, C., et al., "Synthesis and Characterisation of Polyamides Containing 1,4-Dithiin-2,3:5,6-tetrayl Diimide Structures," *Macromol. Rapid Commun. 22*:25-29, Wiley-VCH Verlag GmbH, Germany (2001).
Gaina, C., "Synthesis and Characterization of New Compounds Containing 1,4-Dithiintetracarboxydiimide Units," *Revue Roumaine de Chimie 50*(7-8):601-607, Romanian Academy, Romania (2005).
Valla, A., et al., "Atypical Oxidation Reaction by Thionyl Chloride: Easy Two-Step Synthesis of *N*-Alkyl-1,4-dithiines," *Synthetic Communications 36*:3591-3597, Taylor & Francis, United States (2006).
Zentz, F., et al., "Syntheses, in vitro antibacterial and antifungal activities of a series of *N*-alkyl, 1,4-dithiines," *Il Farmaco 60*:944-947, Elsevier SAS, France (2005).
English language Abstract of Japanese Patent Publication No. 10-JP 10-251265 A, European Patent Office, espacenet database—Worldwide, Sep. 22, 1998.
International Search Report for International Application No. PCT/EP2011/057829, European Patent Office, Netherlands, mailed on Jun. 16, 2011.

* cited by examiner

*Primary Examiner* — Nyeemah A Grazier
(74) *Attorney, Agent, or Firm* — Sterne, Kessler, Goldstein & Fox P.L.L.C.

(57) ABSTRACT

The present invention relates to a new process for preparing dithiine-tetracarboxy-diimides.

10 Claims, 2 Drawing Sheets

PROCESS FOR PREPARING DITHIINE-TETRACARBOXY-DIIMIDES

BACKGROUND OF THE INVENTION

The present invention relates to a new process for preparing dithiine-tetracarboxy-diimides.

Dithiine-tetracarboxy-diimides as such are already known. It is also known that these dithiine-tetracarboxy-diimides can be used as anthelmintics against internal parasites of animals, more particularly nematodes, and have insecticidal activity (cf. U.S. Pat. No. 3,364,229). It is known, furthermore, that certain dithiine-tetracarboxy-diimides possess antibacterial activity and have a certain activity against human mycoses (cf. Il Farmaco 2005, 60, 944-947). It is also known that dithiine-tetracarboxy-diimides can be used as fungicides against phytopathogenic fungi in crop protection (cf. WO 2010/043319). It is known, furthermore, that dithiine-tetracarboxy-diimides can be used as pigments in electrophotographic photoreceptors or as dyes in paints and polymers (cf. JP-A 10-251265, PL-B 143804).

Dithiine-tetracarboximides of the formula (I)

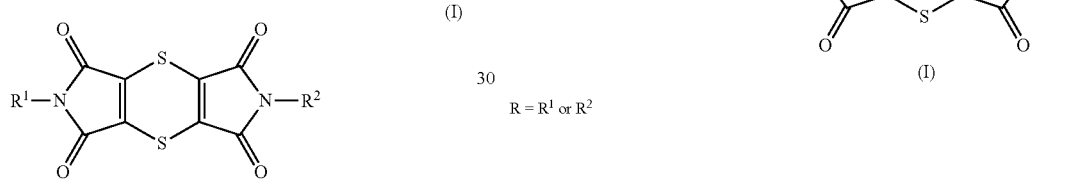

in which $R^1$ and $R^2$ are identical or different and are hydrogen, or are $C_1$-$C_8$-alkyl which is optionally substituted one or more times by halogen, —$OR^3$, and/or —$COR^4$, are $C_3$-$C_7$-cycloalkyl which is optionally substituted one or more times by halogen, $C_1$-$C_4$-alkyl or $C_1$-$C_4$-haloalkyl, or are aryl or aryl-($C_1$-$C_4$-alkyl) each of which is optionally substituted one or more times by halogen, $C_1$-$C_4$-alkyl, $C_1$-$C_4$-haloalkyl, —$COR^4$ or sulphonylamino, $R^3$ is hydrogen, $C_1$-$C_4$-alkyl or $C_1$-$C_4$-alkylcarbonyl or is aryl which is optionally substituted one or more times by halogen, $C_1$-$C_4$-alkyl or $C_1$-$C_4$-haloalkyl, $R^4$ is hydroxyl, $C_1$-$C_4$-alkyl or $C_1$-$C_4$-alkoxy, can be prepared in a variety of known ways.

For example, in one known process (cf. Synthetic Communications 2004, 36, 3591-3597), in a first stage, succinic anhydride is reacted with an amine of the formula (II), optionally in the presence of a diluent. Subsequently, the resultant succinic monoamides of the formula (III) are then reacted with a large excess of thionyl chloride in the presence of dioxane as diluent at room temperature, to give, finally, in a sequence of numerous reaction steps, the dithiine-tetracarboxy-diimides of the formula (I). The dithiine-tetracarboxy-diimides are optionally isolated directly from the reaction mixture or by filtration following addition of water. Depending on reaction conditions (diluents) and the nature of the radicals R, it is possible in certain circumstances to isolate the dithiine-diisoimides of the formula (IV) before they are converted into the dithiine-tetracarboxy-diimides of the formula (I):

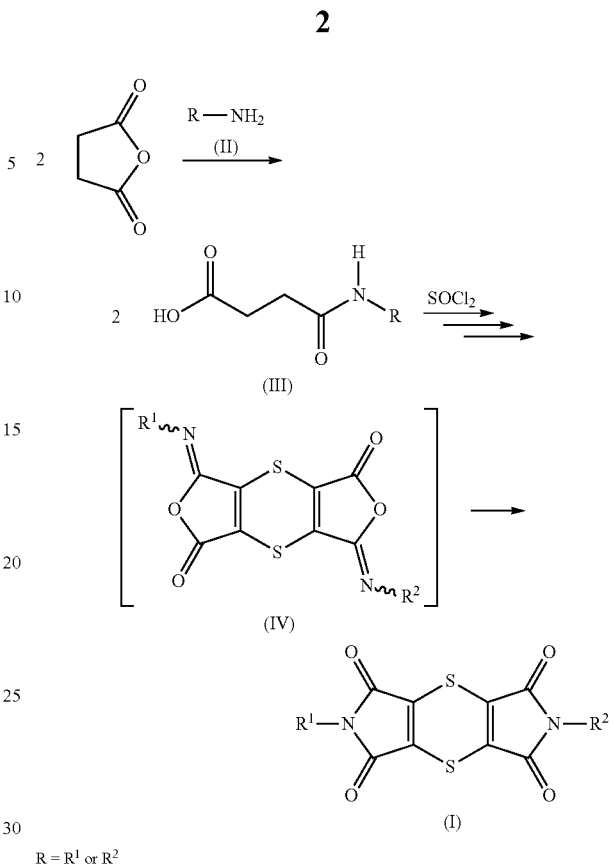

$R = R^1$ or $R^2$

Disadvantages of this process are the long reaction time and also the outcome where either the yields obtained generally do not exceed about 30-40% of theory or else the purities of the isolated products are inadequate. A further disadvantage, in the case of aqueous work-up of the reaction mixture, is that it involves destroying large amounts of thionyl chloride; the gases formed ($SO_2$ and HCl) have to be disposed of. Likewise a disadvantage is the fact that, from experience, the product is not obtained in one portion. Instead, it is frequently the case that, following initial isolation of product by filtration, further product precipitates from the filtrate after prolonged standing (overnight, for example), and must be isolated again by filtration. Occasionally this operation must be carried out once more. This procedure is very laborious and time-consuming.

In another known process (cf. U.S. Pat. No. 3,364,229; Chem. Ber. 1967, 100, 1559-70), in a first stage, dichloromaleic anhydride of the formula (V) is reacted with an amine of formula (II), optionally in the presence of a diluent. Subsequently, the resultant dichloromaleimides of the formula (VI) are then reacted with a sulphur donor compound (for example hydrogen sulphide, thiourea or sodium thiosulphate):

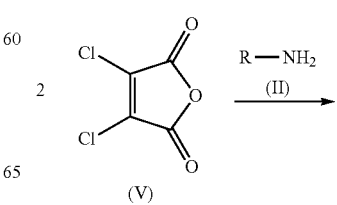

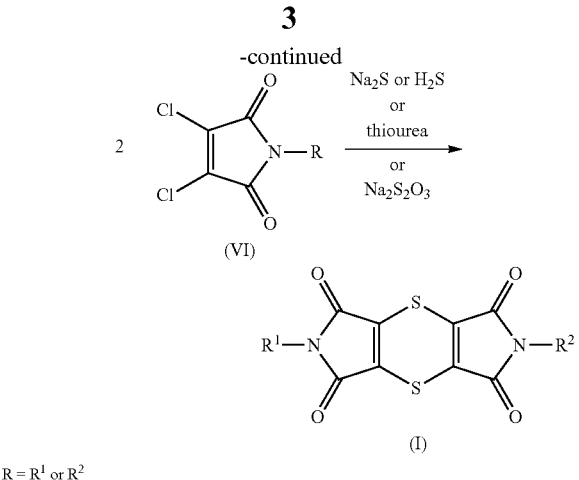

(VI)

R = R¹ or R²

This process has the disadvantages that, for example, operating with the highly toxic gaseous hydrogen sulphide is from a technical standpoint very difficult, costly and inconvenient. When thiourea is used, unwanted by-products are obtained along with the target product, and are very difficult to remove and detract from the attainable yields. If sodium thiosulphate is used, the yield described is insufficient for an industrial operation. Similar considerations apply in respect of the embodiment of the reaction that is described in U.S. Pat. No. 3,364,229, with sodium sulphide (see Example Xb therein).

The preparation of certain dithiine-tetracarboxy-diimides of the formula (I) by reaction of the corresponding dichloromaleimide of the formula (VI) with sodium sulphide is also known, furthermore, from Revue Roumaine de Chimie 2005, 50, 601-607. Here as well, however, the yields are inadequate.

Consequently there continues to be a need for a technically simple and economic preparation process for dithiine-tetracarboxy-diimides of the formula (I).

BRIEF SUMMARY OF THE INVENTION

A new process has now been found for preparing dithiine-tetracarboxy-diimides of the general formula (I)

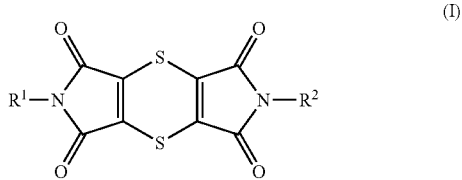

(I)

in which $R^1$ and $R^2$ have the definitions indicated above, characterized in that
(A) dichloromaleimides of the formula (VI)

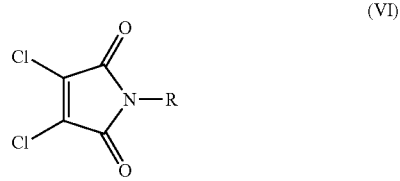

(VI)

in which R is $R^1$ or $R^2$
are reacted with an inorganic sulphide or hydrogen sulphide in a solvent or solvent mixture in a molar ratio between 0.8 and 1.2 mol of sulphide or hydrogen sulphide per mole of dichloromaleimide of the formula (VI).

DETAILED DESCRIPTION OF THE INVENTION

Figure 1:
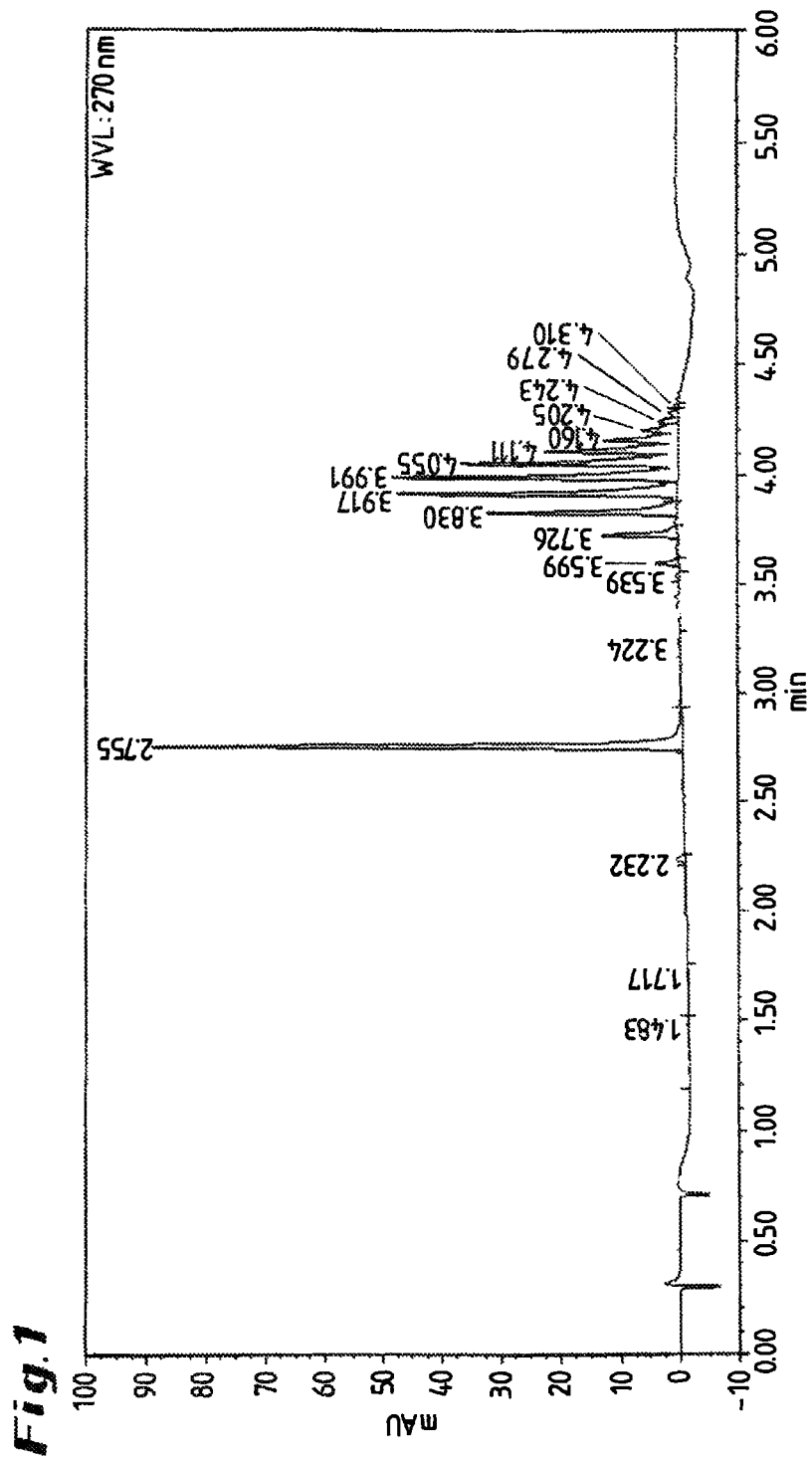
FIG. 1 shows the HPLC analysis (270 nm) for Example 6.

A general definition of the dichloromaleimides used as starting materials when carrying out the process (A) of the invention is provided by the formula (VI). R stands for the definitions of $R^1$ or $R^2$.

$R^1$ and $R^2$ are preferably identical or different and preferably are hydrogen, or are $C_1$-$C_6$-alkyl which is optionally substituted one or more times by fluorine, chlorine, bromine, —$OR^3$ and/or —$COR^4$, or are $C_3$-$C_7$-cycloalkyl which is optionally substituted one or more times by chlorine, methyl or trifluoromethyl, or are phenyl or phenyl($C_1$-$C_4$-alkyl) each of which is optionally substituted one or more times by fluorine, chlorine, bromine, methyl, trifluoromethyl, —$COR^4$ and/or sulphonylamino.

$R^1$ and $R^2$ are also preferably identical or different and preferably are hydrogen, or are $C_1$-$C_6$-alkyl which is optionally substituted one or more times by fluorine, chlorine, bromine and/or —$OR^3$, or are $C_3$-$C_7$-cycloalkyl which is optionally substituted one or more times by chlorine, methyl or trifluoromethyl.

$R^1$ and $R^2$ are more preferably identical or different and more preferably are hydrogen, or are $C_1$-$C_4$-alkyl which is optionally substituted one or more times by fluorine, chlorine, hydroxyl, methoxy, ethoxy, methylcarbonyloxy and/or carboxyl, or are $C_3$-$C_7$-cycloalkyl which is optionally substituted one or more times by chlorine, methyl or trifluoromethyl, or are phenyl, benzyl, 1-phenethyl, 2-phenethyl or 2-methyl-2-phenethyl each of which is optionally substituted one to three times by fluorine, chlorine, bromine, methyl, trifluoromethyl, —$COR^4$ and/or sulphonylamino.

$R^1$ and $R^2$ are more preferably identical or different and more preferably are hydrogen, or are $C_1$-$C_4$-alkyl which is optionally substituted one or more times by fluorine, chlorine, hydroxyl, methoxy and/or ethoxy or are $C_3$-$C_7$-cycloalkyl which is optionally substituted one or more times by chlorine, methyl or trifluoromethyl.

$R^1$ and $R^2$ are very preferably identical or different and very Preferably are hydrogen, methyl, ethyl, n-propyl, isopropyl, 2,2-difluoroethyl or 2,2,2-trifluoroethyl or are cyclopropyl or cyclohexyl each of which is optionally substituted by chlorine, methyl or trifluoromethyl.

$R^1$ and $R^2$ are more particularly preferably simultaneously methyl.

$R^3$ is preferably hydrogen, methyl, ethyl, methylcarbonyl or ethylcarbonyl or is phenyl which is optionally substituted one or more times by fluorine, chlorine, methyl, ethyl, n-propyl, isopropyl or trifluoromethyl.

$R^3$ is more preferably hydrogen, methyl, methylcarbonyl or phenyl.

$R^4$ preferably is hydroxyl, methyl, ethyl, methoxy or ethoxy.

$R^4$ is more preferably hydroxyl or methoxy.

As starting material it is particularly preferred to use N-methyldichloromaleimide (VI-1), R=Me, giving as the end product the compound (I-1) 2,6-dimethyl-1H,5H-[1,4]dithiino[2,3-c:5,6-c']dipyrrole-1,3,5,7(2H,6H)-tetrone.

If dichloromaleimides of the formula (VI) are reacted with a molar deficit amount of sulphide or hydrogen sulphide, polymeric compounds are obtained of the general formula (VII)

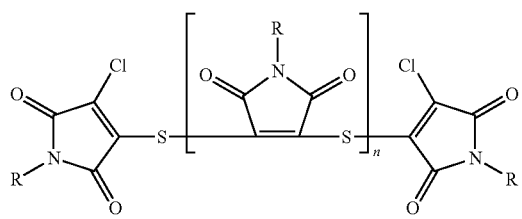

(VII)

in which
to R independently at each occurrence is R$^1$ or R$^2$, and
n is an integer between 1 and 50.

Polymeric compounds of the general formula (VII) are new and likewise provided by the present invention. n is preferably 1 to 25, more preferably 2 to 20, very preferably 3 to 15.

As sulphide or hydrogen sulphide it is possible in principle to use all soluble inorganic sulphides or hydrogen sulphides, such as, for example, lithium sulphide, sodium sulphide, sodium hydrogen sulphide, potassium sulphide, calcium sulphide, calcium hydrogen sulphide, magnesium sulphide or ammonium sulphide. It is preferred to use sodium sulphide, potassium sulphide or ammonium sulphide. It is of course also possible to use mixtures of these salts. The terms "sulphide" and "hydrogen sulphide" are also intended to encompass hydrates of these salts, where they exist.

For the preparation of the dithiine-tetracarboxy-diimides of the formula (I), the sulphide or hydrogen sulphide is used in amounts between 0.8 and 1.2 mol per mole of dichloromaleimide of the formula (VI). Preferred amounts are between 0.9 and 1.1 mol, more preferably between 0.95 and 1.05 mol, very preferably 1 mol of sulphide or hydrogen sulphide, per mole of dichloromaleimide of the formula (VI).

For the preparation of the polymeric compounds of the general formula (VII), the sulphide or hydrogen sulphide is used in amounts between 0.2 and 0.95 mol per mole of dichloromaleimide of the formula (VI). Preferred amounts are between 0.4 and 0.9 mol, more preferably between 0.5 and 0.8 mol, per mole of dichloromaleimide of the formula (VI).

The sulphide or hydrogen sulphide can be added to the reaction mixture in solid form or as a solution, in water, for example. It is preferred to add the sulphide or hydrogen sulphide as a solution in water.

The reaction temperature in process (A) of the invention can be varied within wide limits and lies between −20° C. and 140° C. In order to obtain satisfactory space-time yields, it is preferred to operate at temperatures between −10 and 100° C., more preferably between 0 and 50° C.

The reaction time in process (A) of the invention is between 5 minutes and 24 hours. It is preferred to operate for between 10 minutes and 12 hours, more preferably between 20 minutes and 2 hours.

Suitable solvents for process (A) of the invention include water, dimethyl sulphoxide, sulpholane, alcohols such as methanol, ethanol, propanol, isopropanol, butanol, tert-butanol, cyclopentanol, cyclohexanol, ethylene glycol and ethylene glycol monomethyl ether, esters such as methyl acetate and ethyl acetate, amides such as formamide, N,N-dimethylformamide, N,N-dimethylacetamide and N-methylpyrrolidone, ethers such as tetrahydrofuran and 1,4-dioxane, nitriles such as acetonitrile, propionitrile, butyronitrile and benzonitrile, ketones such as acetone, methyl ethyl ketone, methyl isobutyl ketone and pinacolone, or mixtures of these diluents. It is preferred to use water, dimethyl sulphoxide, methanol, ethanol, propanol, isopropanol, butanol, tert-butanol, cyclohexanol, ethylene glycol, methyl acetate, N,N-dimethylformamide, N,N-dimethylacetamide, tetrahydrofuran, 1,4-dioxane, acetonitrile, acetone, methyl ethyl ketone, methyl isobutyl ketone, or mixtures of these diluents. It is very preferred to use mixtures of water and methanol, ethanol, propanol, isopropanol, methyl acetate, tetrahydrofuran, 1,4-dioxane, acetonitrile or acetone.

A further process (B) of the invention for preparing dithiine-tetracarboxy-diimides of the general formula (I) involves heating a product of the reaction of the dichloromaleimide of the formula (VI) with a sulphide or hydrogen sulphide, composed wholly or partly of compounds of the formula (VII), in a suitable diluent.

Suitable diluents for carrying out process (B) of the invention are polar solvents; examples here include amides such as formamide, N,N-dimethylformamide, N,N-dimethylacetamide and N-methylpyrrolidone; alcohols such as propanol, isobutanol, pentanol and ethylene glycol; esters such as methyl acetate, ethyl acetate and butyl acetate; nitriles such as acetonitrile and butyronitrile; ketones such as pinacolone and methyl isobutyl ketone; dimethyl sulphoxide or sulpholane, or water. These diluents may be used alone or in a mixture with water.

The amount of solvent is not critical and can be varied within wide limits.

Process (B) of the invention is carried out at temperatures between 0 and 200° C. Preferred temperatures are between 20 and 250° C.

The processes of the invention are illustrated by, but not confined to, the following examples.

PREPARATION EXAMPLES

Example 1

A 2 liter jacketed vessel was charged with 250 ml of methanol and 50 ml of water. Metered in simultaneously over the course of 1 hour at 21° C. were, first, a solution of 90 g [0.5 mol] of to N-methyldichloromaleimide (VI-1) in 700 ml of methanol and, second, a solution of 66.05 g [0.5 mol] of sodium sulphide trihydrate in 200 ml of water. The mixture was subsequently stirred at room temperature for a further 30 minutes. The solid was isolated by suction, washed with twice 300 ml of water and then twice 300 ml of methanol, and dried. This gave 64.49 g of a black-green solid, which according to HPLC analysis against reference material is composed to an extent of 95.1 percent by weight of the compound (I-1), corresponding to a yield of 86.9% of theory.

Example 2

A solution of 4.5 g [25 mmol] of N-methyldichloromaleimide (VI-1) in 65 ml of methanol was admixed dropwise at room temperature with a solution of 3.30 g [25 mmol] of sodium sulphide trihydrate in 10 ml of water. The mixture was subsequently stirred at room temperature for a further 4 hours. The solid was isolated by suction, washed with 15 ml of water and then 15 ml of methanol, and dried. This gave 3.00 g of a pale green solid, which according to HPLC analysis is composed to an extent of 93.6 area percent of the compound (I-1), corresponding to a yield of 79.6% of theory.

Example 3

A 2 liter jacketed vessel was charged with 250 ml of methanol and 50 ml of water. Metered in simultaneously over the course of 1 hour at 10° C. were, first, a solution of 90 g [0.5 mol] of N-methyldichloromaleimide (VI-1) in 700 ml of methanol and, second, 85.2 g of 40% strength aqueous ammonium sulphide solution [0.5 mol], diluted with 176 ml of water. The mixture was subsequently stirred at 10° C. for a further 30 minutes. Then the solid was isolated directly by suction, washed with twice 300 ml of water and then twice 300 ml of methanol, and dried. This gave 64.10 g of a black-green solid, which according to HPLC analysis against reference material is composed to an extent of 94.4 percent by weight of the compound (I-1), corresponding to a yield of 85.8% of theory.

Example 4

The procedure described in Example 3 was followed, but using 0.525 mol of ammonium sulphide. This gave 63.56 g of a black-green solid, which according to HPLC analysis against reference material is composed to an extent of 96.3 percent by weight of the compound (I-1), corresponding to a yield of 86.7% of theory.

Example 5

The procedure described in Example 3 was followed, but using 0.55 mol of ammonium sulphide. This gave 57.62 g of a black-green solid, which according to HPLC analysis against reference material is composed to an extent of 93.8 percent by weight of the compound (I-1), corresponding to a yield of 76.8% of theory.

Example 6

A 500 ml flask was charged with a solution of 18 g [0.1 mol] of N-methyldichloromaleimide (VI-1) in 260 ml of methanol. Then, at 14-16° C., a solution of 6.61 g [0.05 mol] of sodium sulphide trihydrate in 40 ml was added dropwise. The mixture was allowed to come to room temperature over the course of 55 minutes and was stirred at room temperature for a further 60 minutes. The solid was then isolated with suction, washed with 60 ml of water, and dried. This gave 7.05 g of a green solid which according to HPLC analysis (270 nm) is composed to an extent of 75.1 area percent of the compound (I-1). Additionally, a total of around 22.5 area percent of the compound of the formula (VII) in which R is methyl is found (cf. FIG. 1).

The compounds of the formula (VII) (R=methyl) were isolated by preparative HPLC.

Figure 2:
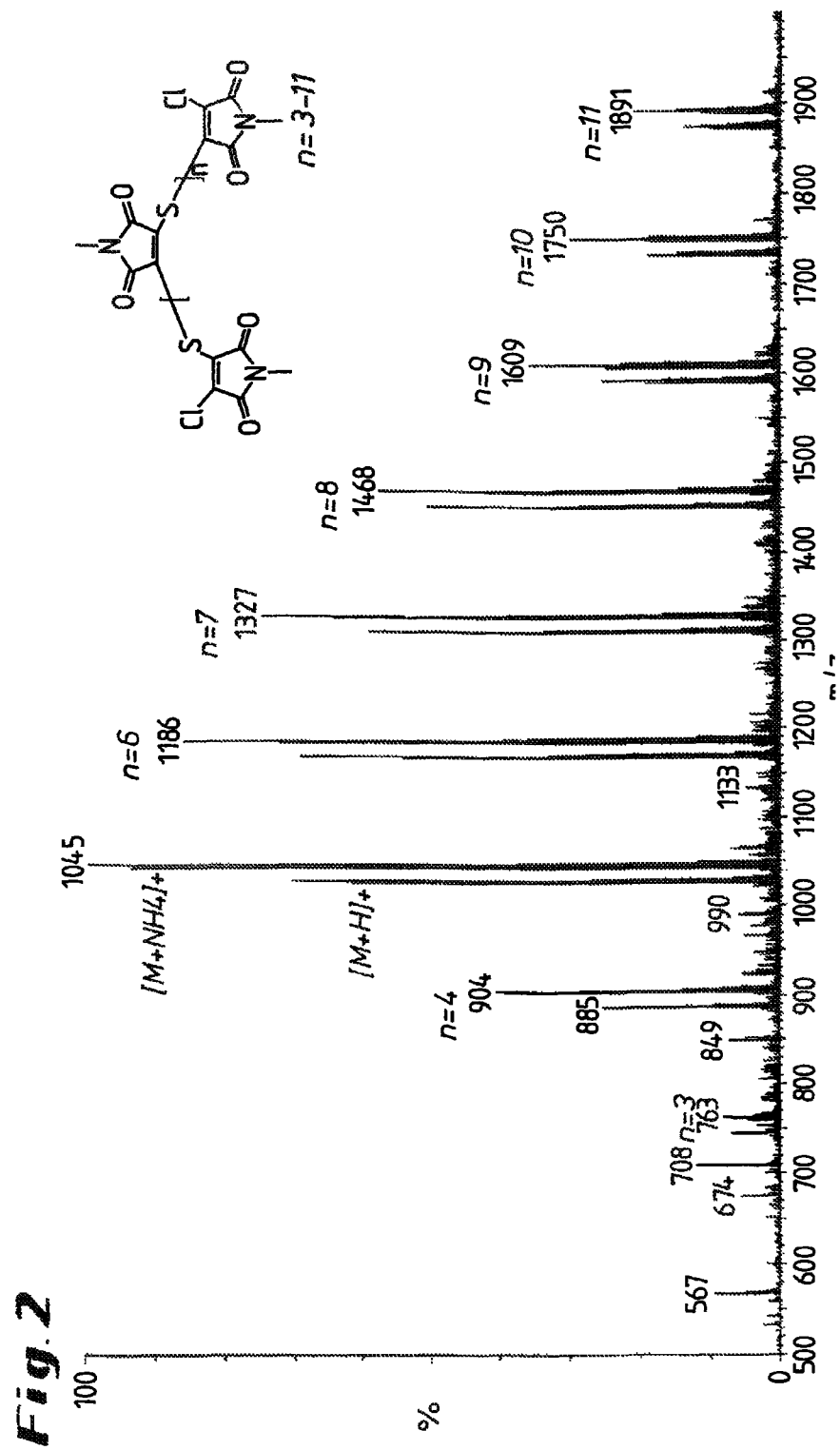
FIG. 2 shows the EM⁺ mass spectrum for Example 6.

The ESI$^+$ mass spectrum of the compounds of the formula (VII) with R=methyl was obtained by adding together the mass spectra in the mass range of 500-2000 Da in the 3.5-4.5 min retention time range. Apparent in this mass range are the quasi-molecular ions ([M+H]$^+$ and [M+NH$_4$]$^+$) of the oligomers with n=3-11 (cf. FIG. 2).

Example 7

Of the product mixture from Example 6, 2 g were heated in a mixture of 20 ml of ethanol and 2 ml of dimethyl sulphoxide at 77° C. for 2 hours. The solvent mixture was subsequently removed under reduced pressure, and the residue was taken up in 10 ml of methanol, and the solid was isolated with suction, washed with 5 ml of MeOH and dried. This gave 1.77 g of green solid, which according to HPLC analysis (270 nm) is composed to an extent of 93 area percent of the compound (I-1).

Example 8

Of a product mixture with 64.4 percent by weight of the compound (I-1), 2 g were heated in 10 ml of dimethyl sulphoxide at 100° C. for 2 hours. The reaction mixture was subsequently admixed with 30 ml of methanol, and the solid was isolated with suction, washed with 5 ml of methanol and dried. This gave 1.441 g of a black-green solid which is composed to an extent of 99.4 percent by weight of the compound (I-1).

Example 9

Of a product mixture with 64.4 percent by weight of the compound (I-1), 2 g were heated in 20 ml of butyronitrile under reflux (117° C.) for 2 hours. Subsequently the solvent was removed under reduced pressure, the residue was admixed with 10 ml of methanol, and the solid was isolated with suction, washed with 5 ml of methanol and dried. This gave 1.694 g of a green solid which is composed to an extent of 92 percent by weight of the compound (I-1).

Comparative Example 1

A 2 liter jacketed vessel was charged with 250 ml of methanol and 50 ml of water. Metered in simultaneously over the course of 1 hour at 21° C. were, first, a solution of 90 g [0.5 mol] of N-methyldichloromaleimide (VI-1) in 700 ml of MeOH and, second, a solution of 79.25 g [0.6 mol] of sodium sulphide trihydrate in 200 ml of water. The mixture was subsequently stirred at room temperature for a further 30 minutes. The solid was isolated by suction, washed with twice 300 ml of water and then twice 300 ml of methanol, and dried. This gave 19.97 g of a pale-green solid, which according to HPLC analysis is composed to an extent of 99.9 area % of the compound (I-1), corresponding to a yield of 28.3% of theory.

Comparative Example 2

The procedure described in Example 2 was repeated, but using 3.96 g [30 mmol] of sodium sulphide trihydrate. After 4 hours at room temperature, no solid remained after the reaction mixture was filtered; in other words, the isolated yield was 0% of theory.

We claim:
1. A process for preparing the compound of formula (I)

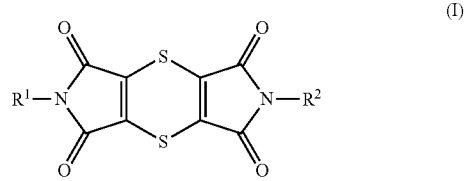

in which
R$^1$ and R$^2$ are identical or different and are hydrogen, or are C$_1$-C$_8$-alkyl which is optionally substituted one or more times by halogen, —OR$^3$ or —COR$^4$, or are C$_3$-C$_7$-cycloalkyl which is optionally substituted one or more times by halogen, C$_1$-C$_4$-alkyl or C$_1$-C$_4$-haloalkyl, or are aryl or aryl-(C$_1$-C$_4$-alkyl) each of which is optionally substituted one or more times by halogen, C$_1$-C$_4$-alkyl, C$_1$-C$_4$-haloalkyl, —COR$^4$ or sulphonylamino,
R$^3$ is hydrogen, C$_1$-C$_4$-alkyl or C$_1$-C$_4$-alkylcarbonyl or is aryl which is optionally substituted one or more times by halogen, C$_1$-C$_4$-alkyl or C$_1$-C$_4$-haloalkyl, and
R$^4$ is hydroxyl, C$_1$-C$_4$-alkyl or C$_1$-C$_4$-alkoxy,
said process comprises reacting
(A) a compound of formula (VI)

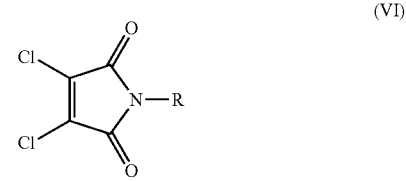

in which R is R$^1$ or R$^2$ are defined above
with an inorganic sulphide or hydrogen sulphide in a solvent or solvent mixture in a molar ratio between 0.2 and 0.95 mol of sulphide or hydrogen sulphide per mole of the compound of formula (VI) to form a reaction product, and (B) heating the reaction product, which is composed of a mixture of at least on compound of formula (I) and at least one compound of formula (VII)

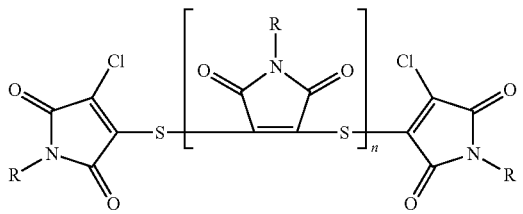

(VII)

in which
R independently at each occurrence is $R^1$ or $R^2$ as defined above, and
n is an integer between 1 and 50,
in a diluent.

2. A compound of formula (VII)

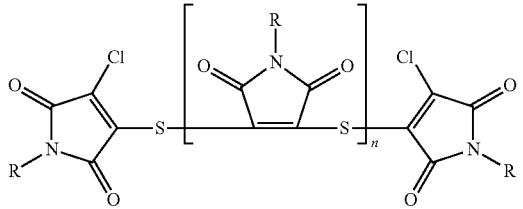

(VII)

in which
R independently at each occurrence is $R^1$ or $R^2$,
$R^1$ and $R^2$ are identical or different and are hydrogen, or are $C_1$-$C_8$-alkyl which is optionally substituted one or more times by halogen, —$OR^3$ or —$COR^4$, or are $C_3$-$C_7$-cycloalkyl which is optionally substituted one or more times by halogen, $C_1$-$C_4$-alkyl or $C_1$-$C_4$-haloalkyl, or are aryl or aryl-($C_1$-$C_4$-alkyl) each of which is optionally substituted one or more times by halogen, $C_1$-$C_4$-alkyl, $C_1$-$C_4$-haloalkyl, —$COR^4$ or sulphonylamino,
$R^3$ is hydrogen, $C_1$-$C_4$-alkyl or $C_1$-$C_4$-alkylcarbonyl or is aryl which is optionally substituted one or more times by halogen, $C_1$-$C_4$-alkyl or $C_1$-$C_4$-haloalkyl,
$R^4$ is hydroxyl, $C_1$-$C_4$-alkyl or $C_1$-$C_4$-alkoxy,
n is an integer between 1 and 50.

3. The process according to claim 1, wherein the sulphide or hydrogen sulphide is lithium sulphide, sodium sulphide, sodium hydrogen sulphide, potassium sulphide, calcium sulphide, calcium hydrogen sulphide, magnesium sulphide or ammonium sulphide or mixtures thereof or hydrates thereof.

4. The process according to claim 1, wherein a polar solvent is used as diluent in process step (B).

5. The process according to claim 4, wherein the solvent is an amide, a nitrile, a ketone, dimethyl sulphoxide, sulpholane or water, either used alone or in mixtures with water.

6. The process according to claim 5, wherein the amide is selected from the group consisting of formamide, N,N-dimethylformamide, N,N-dimethylacetamide, and N-methylpyrrolidone.

7. The process according to claim 5, wherein the alcohol is selected from the group consisting of propanol, isobutanol, pentanol, and ethylene glycol.

8. The process according to claim 5, wherein the ester is selected from the group consisting of methyl acetate, ethyl acetate, and butyl acetate.

9. The process according to claim 5, wherein the nitrile is selected from the group consisting of acetonitrile, and butyronitrile.

10. The process according to claim 5, wherein the ketone is selected from the group consisting of pinacolone, and methyl isobutyl ketone.

* * * * *